United States Patent
Cheng et al.

(10) Patent No.: US 12,427,041 B1
(45) Date of Patent: Sep. 30, 2025

(54) KNEE JOINT STRUCTURE FEATURING HYDRAULIC CONTROL

(71) Applicant: Ken Dall Enterprise Co., Ltd., New Taipei (TW)

(72) Inventors: Chia-Pao Cheng, New Taipei (TW); Hsiang-Ming Wu, New Taipei (TW); Chih-Hsuan Liang, New Taipei (TW)

(73) Assignee: KEN DALL ENTERPRISE CO., LTD., New Taipei (TW)

( * ) Notice: Subject to any disclaimer, the term of this patent is extended or adjusted under 35 U.S.C. 154(b) by 23 days.

(21) Appl. No.: 18/614,769

(22) Filed: Mar. 25, 2024

(51) Int. Cl.
    *A61F 2/64*     (2006.01)
    *A61F 2/74*     (2006.01)

(52) U.S. Cl.
    CPC ............... *A61F 2/64* (2013.01); *A61F 2/74* (2021.08); *A61F 2/748* (2021.08)

(58) Field of Classification Search
    CPC ...... A61F 2/38; A61F 2/30; A61F 2/46; A61F 2/64; A61F 2/644
    See application file for complete search history.

(56) References Cited

U.S. PATENT DOCUMENTS

| | | | |
|---|---|---|---|
| 7,066,964 B2 * | 6/2006 | Wild | A61F 2/68 623/46 |
| 9,005,309 B2 * | 4/2015 | Wu | A61F 2/68 623/39 |
| 9,089,443 B2 * | 7/2015 | Shirata | A61F 2/76 |

* cited by examiner

*Primary Examiner* — Christopher J Beccia
(74) *Attorney, Agent, or Firm* — Leong C. Lei

(57) ABSTRACT

A knee joint structure featuring hydraulic control includes a knee-joint base having a receiving space, an upper fluid channel, a lower fluid channel and a common channel; a hydraulic axle core arranged in the receiving space; a fluid barrier block arranged on an internal wall of the knee-joint base and in contact with the hydraulic axle core to divide the receiving space into upper and lower fluid chambers. The upper and lower fluid chambers are respectively in communication with the upper and lower fluid channels. The fluid barrier block is in communication with the common channel. The cushioning fluid chamber is directly formed in the knee-joint base so that the cost is reduced, and during bending of the knee-joint base, a pressure difference of the upper and lower fluid chambers cause fluid to flow therebetween to realize a hydraulic cushioning effect.

9 Claims, 8 Drawing Sheets

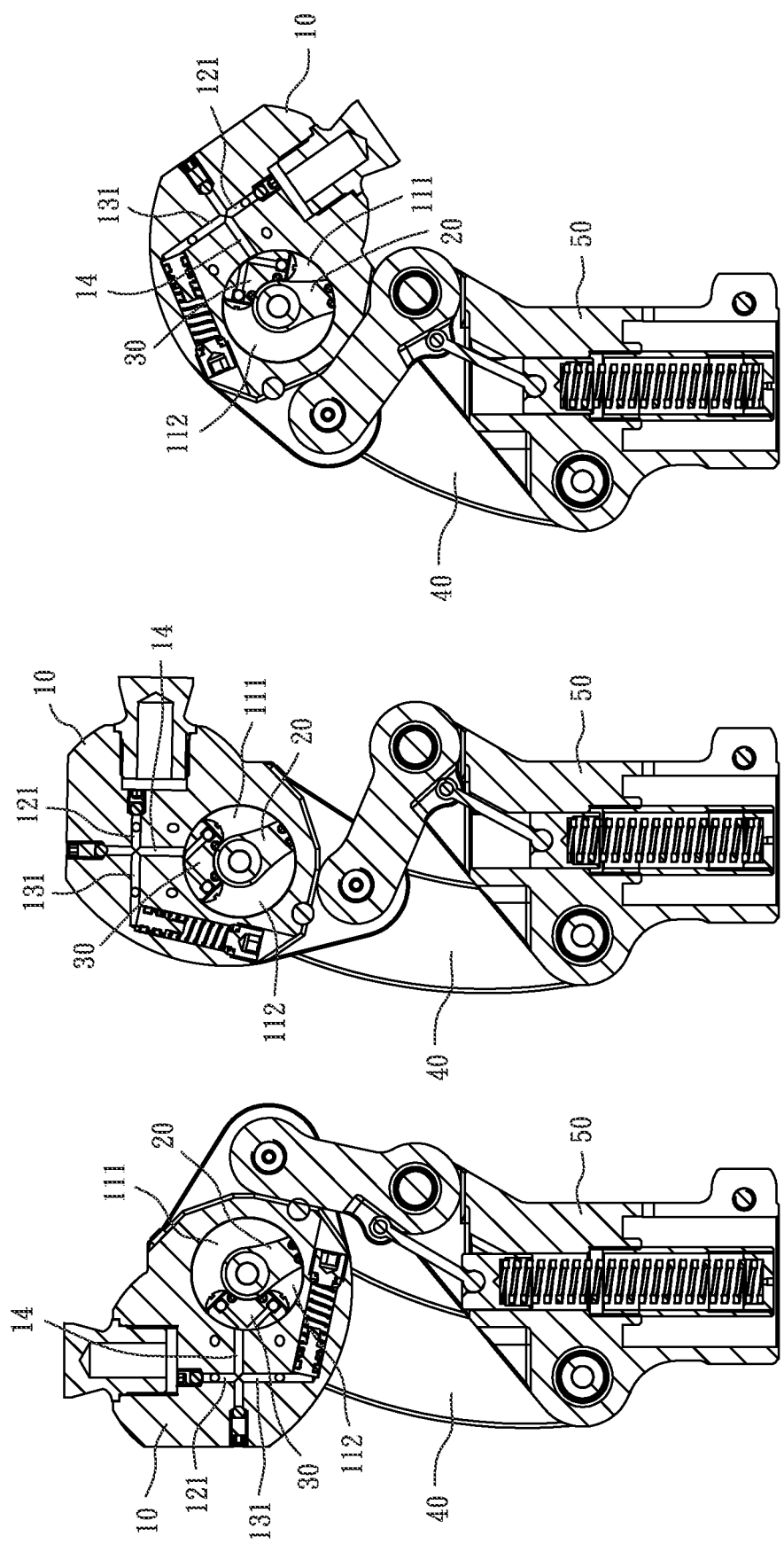

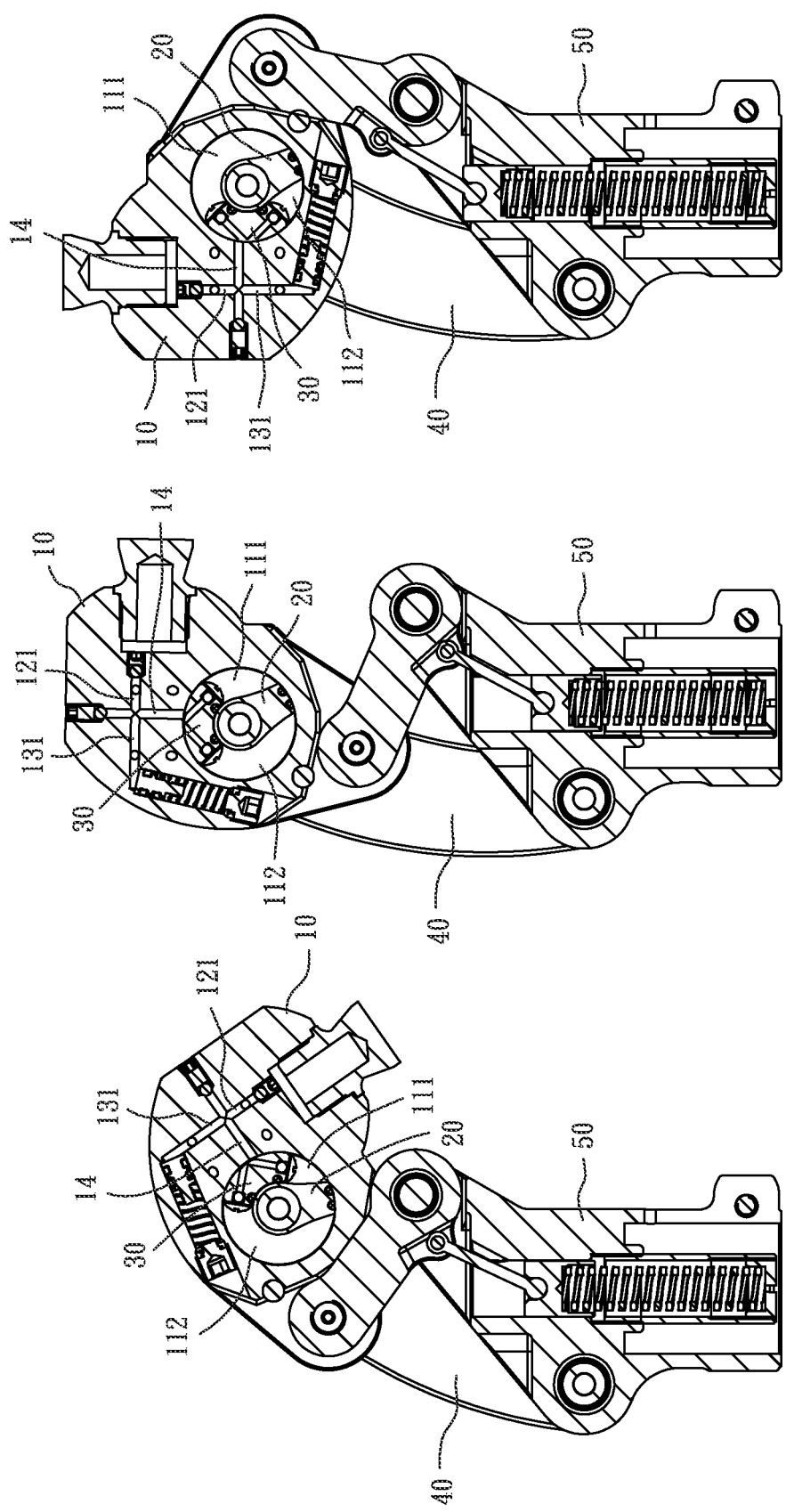

KNEE JOINT STRUCTURE FEATURING HYDRAULIC CONTROL

BACKGROUND OF THE INVENTION

(a) Technical Field of the Invention

The present invention relates to a knee joint structure, and more particularly to a knee joint structure featuring hydraulic control, which, in addition to cost reduction, realizes a hydraulic cushioning effect by means of a pressure difference between upper and lower fluid chambers to enable fluid to flow therebetween.

(b) Description of the Prior Art

A prosthesis is an artificially made limb for replacement of the function of a damaged limb or for modification of an outside appearance of a damaged limb, in which a knee joint is a key factor for designs, because it relates to the gait and kinetic balance of walking and must involve functions of supporting and walking to take the place of a normal knee joint.

A known knee joint structure, as disclosed in US Patent No. U.S. Pat. No. 9,005,309B, includes a cushioning fluid chamber arranged at the site of a push rod axle at a lower side and uses a push rod and a transmission plate to realize a hydraulic cushioning effect during rotation and bending of the knee joint.

However, the structure of the US Patent is relatively complicated, making the fabrication cost relatively high. The structure is thus not perfect and it is a challenge of the manufacturers to improve the shortcomings of the known knee joint.

SUMMARY OF THE INVENTION

An objective of the present invention is to provide a knee joint structure featuring hydraulic control, which, in addition to cost reduction, realizes a hydraulic cushioning effect by means of a pressure difference between upper and lower fluid chambers to enable fluid to flow therebetween.

To achieve the above objective, the present invention provides a knee joint structure featuring hydraulic control, which comprises a knee-joint base, a hydraulic axle core, and a fluid barrier block, wherein the knee-joint base forms a receiving space in an interior thereof, a fluid being received in the receiving space, an upper fluid channel and a lower fluid channel being formed in an internal wall of the knee-joint base at one side of the receiving space, the upper fluid channel and the lower fluid channel being in communication with a common channel; the hydraulic axle core is arranged in the receiving space, two ends of the hydraulic axle core being each connected to one end of a link bar, an opposite end of the link bar being pivotally connected to a pivotal base; and the fluid barrier block is arranged on the internal wall of the knee-joint base and in contact with the hydraulic axle core to divide the receiving space into an upper fluid chamber and a lower fluid chamber, the upper fluid chamber being in communication with the upper fluid channel, the lower fluid chamber being in communication with the lower fluid channel, the fluid barrier block being in communication with the common channel and controlling the fluid to flow unidirectionally from the upper fluid chamber into the lower fluid chamber, or from the lower fluid chamber into the upper fluid chamber.

The present invention forms the cushioning fluid chamber directly in the interior of the knee-joint base, so as to reduce cost and also to allow for direct control the knee-joint base in rotation (counterclockwise or clockwise) and bending such that by means of a pressure difference between the upper fluid chamber and the lower fluid chamber, fluid is caused to flow therebetween to realize an effect of hydraulic cushioning to for example achieve effective cushioning and reducing an impact force that a user has to take during walking, making walking posture natural and easy.

BRIEF DESCRIPTION OF THE DRAWINGS

FIGS. 4-7 are cross-sectional views demonstrating an example of operation of the present invention, illustrating a knee-joint base bending through clockwise rotation.

FIGS. 8-11 are cross-sectional views demonstrating an example of operation of the present invention, illustrating a knee-joint base bending through counterclockwise rotation.

DETAILED DESCRIPTION OF THE PREFERRED EMBODIMENTS

Figure 1:
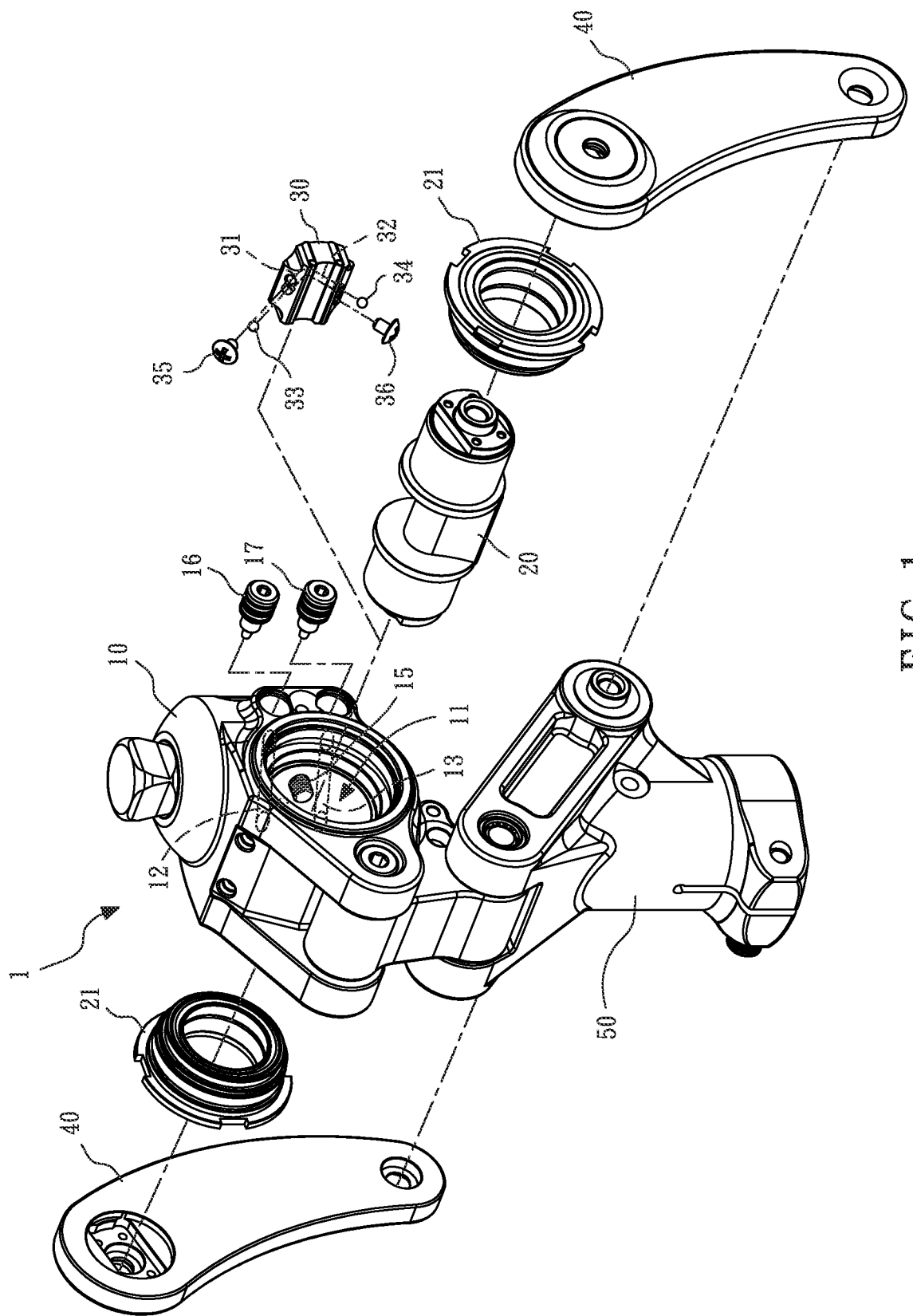
FIG. 1 is an exploded view of the present invention.
Figure 2:
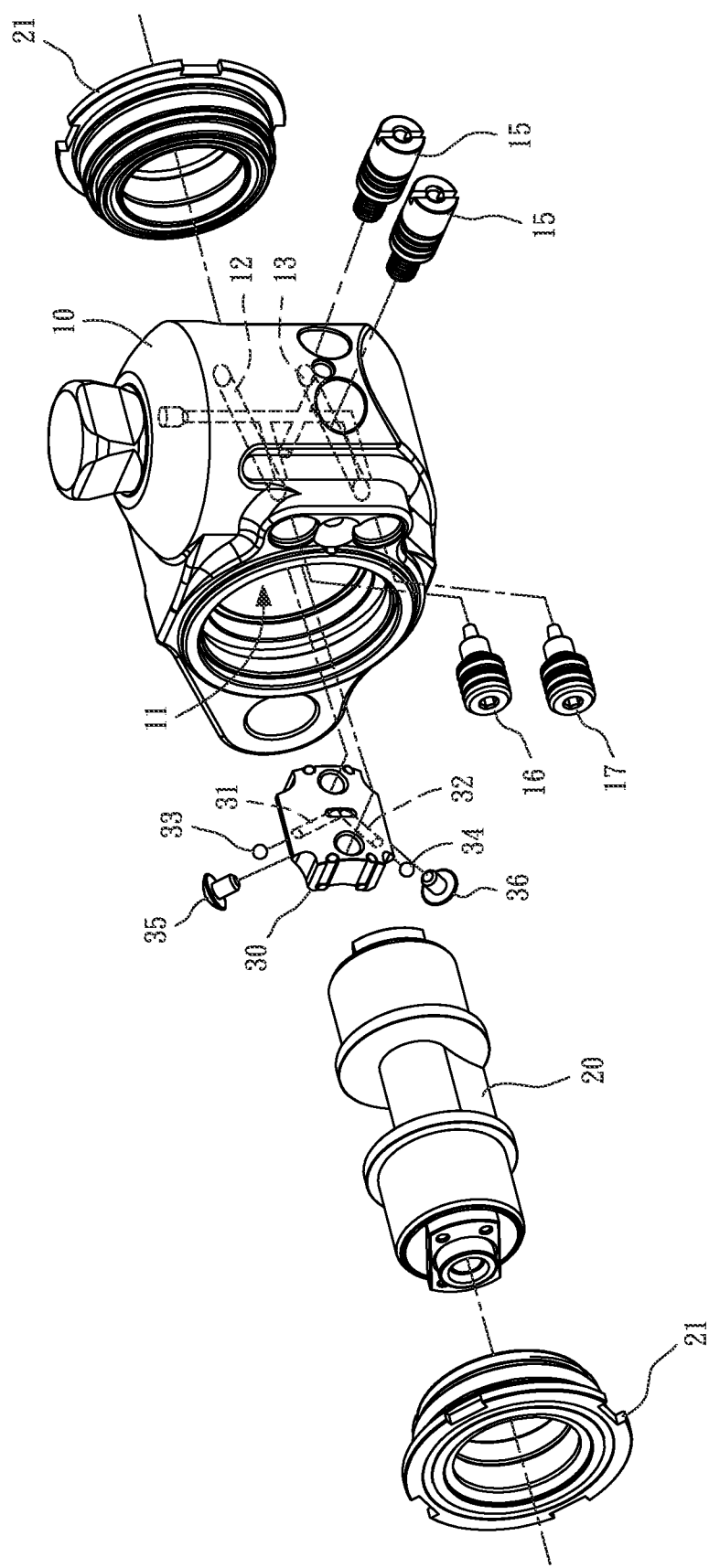
FIG. 2 is an exploded view of the present invention taken from a different side.
Figure 3:
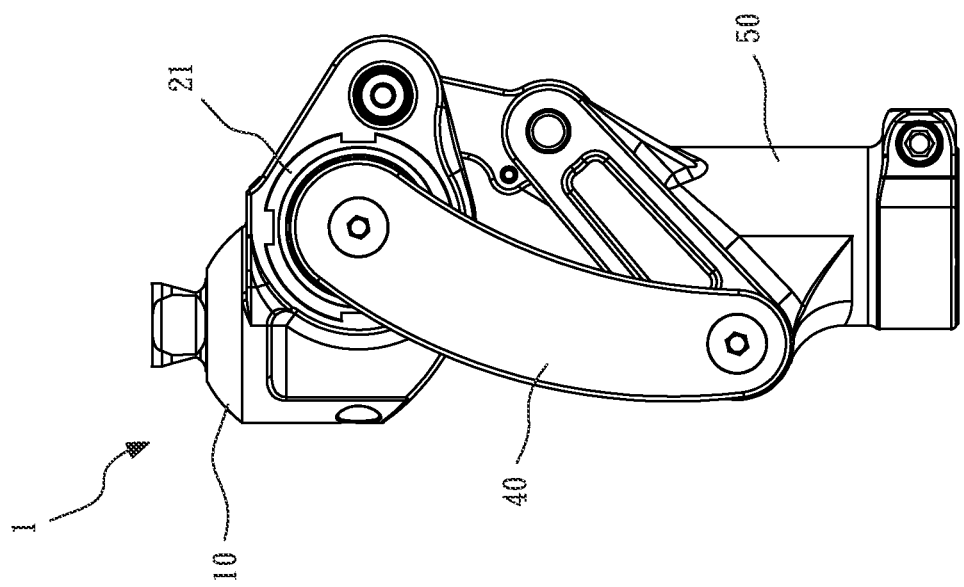
FIG. 3 is a side elevational view of the present invention.
Figure 7:
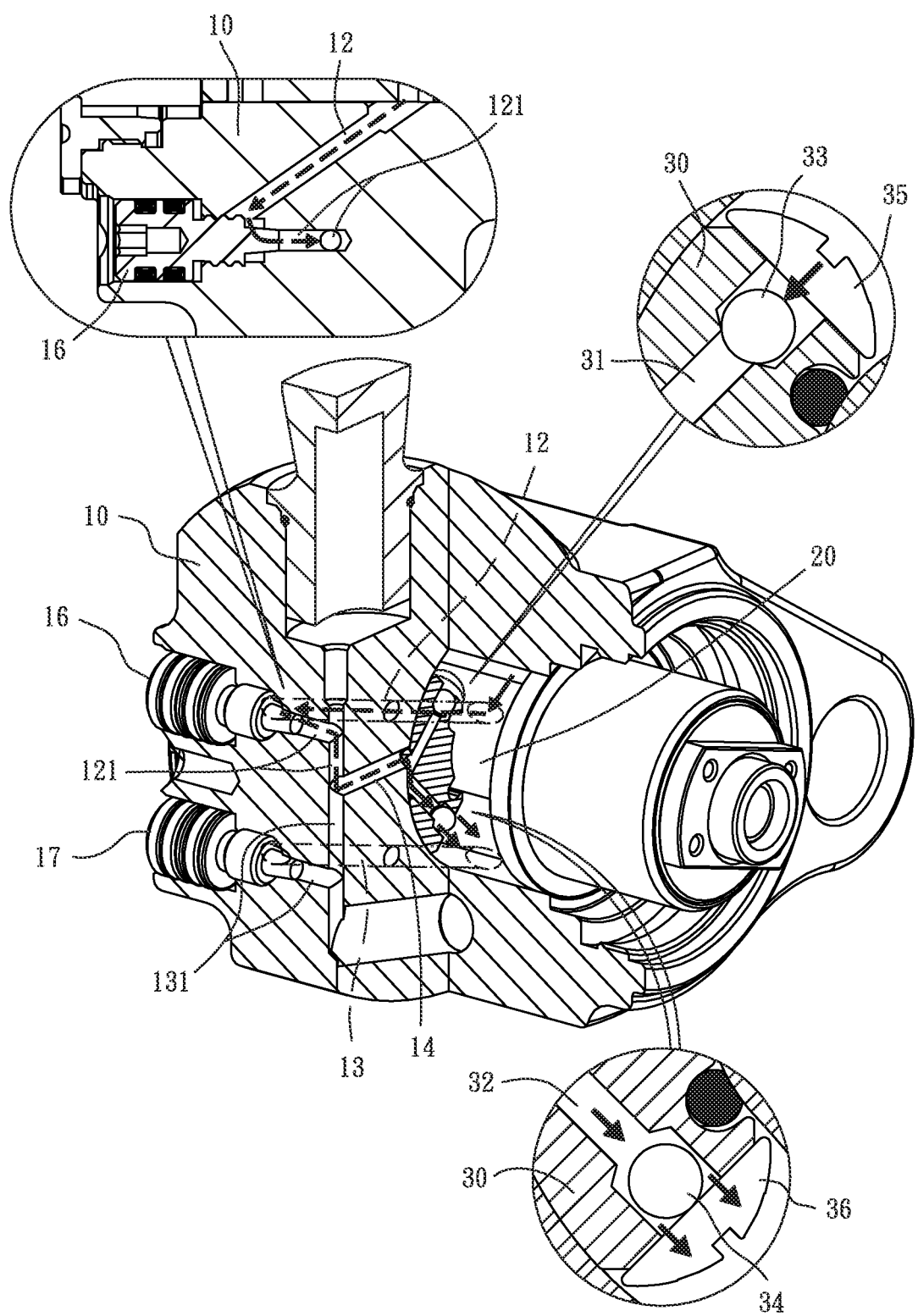

Referring to FIGS. 1-4 and 7, the present invention provides a knee joint structure featuring hydraulic control, generally designated at 1, which comprises a knee-joint base 10, a hydraulic axle core 20, and a fluid barrier block 30. Details are provided below:

The knee-joint base 10 is formed, in an interior thereof, with a receiving space 11 to serve as a cushioning fluid chamber, and a fluid is received and held in the receiving space 11. An upper fluid channel 12 and a lower fluid channel 13 are formed in an internal wall of the knee-joint base 10 at one side of the receiving space 11, and the upper fluid channel 12 and the lower fluid channel 13 are set in communication with a common channel 14.

The hydraulic axle core 20 is disposed in the receiving space 11, and two ends of the hydraulic axle core 20 are end connected to one end of a link bar 40, while an opposite end of the link bar 40 is pivotally connected to a pivotal base 50.

The fluid barrier block 30 is arranged on the internal wall of the knee-joint base 10 and in contact with the hydraulic axle core 20 to divide the receiving space 11 into an upper fluid chamber 111 and a lower fluid chamber 112, wherein the upper fluid chamber 111 is in communication with the upper fluid channel 12, and the lower fluid chamber 112 is in communication with the lower fluid channel 13. The fluid barrier block 30 is in communication with the common channel 14 and controls the fluid to unidirectionally flow from the upper fluid chamber 111 into the lower fluid chamber 112, or from the lower fluid chamber 112 into the upper fluid chamber 111.

In an embodiment, the upper fluid channel 12 is in communication with an upper cruciform channel 121, and the lower fluid channel 13 is in communication with a lower cruciform channel 131, and the upper cruciform channel 121 and the lower cruciform channel 131 are jointly in communication with the common channel 14.

In an embodiment, the fluid comprises one of a hydraulic liquid and a lubricant oil.

In an embodiment, the two ends of the hydraulic axle core 20 are respectively provided with two positioning members 21, and are each connected to the one end of the respective link bar 40 by the positioning members 21.

In an embodiment, the fluid barrier block 30 comprises a first passage 31 and a second passage 32, and one end opening of the first passage 31 is in communication with the upper fluid chamber 111 and is provided with a first one-way valve for controlling opening and closing of the end opening of the first passage 31, and one end opening of the second passage 32 is in communication with the lower fluid chamber 112 and is provided with a second one-way valve for controlling opening and closing of the end opening of the second passage 32, and an opposite end opening of the first passage 31 and an opposite end opening of the second passage 32 are jointly in communication with the common channel 14.

In an embodiment, the first one-way valve is structured such that the one end opening of the first passage 31 is provided with a first spherical bead 33, and the first spherical bead 33 is movably arranged in the one end opening of the first passage 31. The first one-way valve further comprises a first blocking member 35, and the first blocking member 35 functions to block and retain the first spherical bead 33 in position. The second one-way valve is structured such that the one end opening of the second passage 32 is provided with a second spherical bead 34, and the second spherical bead 34 is movably arranged in the one end opening of the second passage 32 for controlling opening and closing of the one end opening of the second passage 32. The second one-way valve further comprises a second blocking member 36, and the second blocking member 36 functions to stop and retain the second spherical bead 34 in position.

In an embodiment, the fluid barrier block 30 is mounted to the internal wall of the knee-joint base 10 by means of two fastening members 15, such as screws.

In an embodiment, the fluid barrier block 30 is integrally formed with the knee-joint base 10 in a one-piece structure.

The above provides an introduction to every component/part of the present invention, and a way of assembling them, and in the following examples of use and advantages and efficacy of the present invention will be described as follows:

Referring to FIGS. 4-7, the present invention uses the hydraulic axle core 20 to divide the cushioning fluid chamber into the upper fluid chamber 111 and the lower fluid chamber 112.

When the knee-joint base 10 is bending through clockwise rotation (as shown in FIGS. 5 and 6), the fluid barrier block 30 is moved therewith to rotate relative to the hydraulic axle core 20. Under this condition, the upper fluid chamber 111 is compressed by the fluid barrier block 30 to get reduced thereby causing a hydraulic pressure inside the upper fluid chamber 111 to increase and compressing and driving the fluid to flow toward the lower fluid chamber 112, in which a flow path is as follows:

The increase of the hydraulic pressure inside the upper fluid chamber 111 compresses and forces the fluid to flow into the upper fluid channel 12 to thus pass through the upper cruciform channel 121 and the common channel 14 to flow into the fluid barrier block 30, and the first spherical bead 33 provided on the fluid barrier block 30 is located in the upper fluid chamber 111, so that due to the hydraulic pressure inside the upper fluid chamber 111 being made relatively large, the first spherical bead 33 is pressed down by the hydraulic pressure to become blocking and thus closing the one end opening of the first passage 31. Under this condition, the lower fluid chamber 112 has a relatively small pressure and this makes the second spherical bead 34 departing and thus opening the one end opening of the second passage 32. Thus, the fluid directly flows out of the one end opening of the second passage 32 on the lower side of the fluid barrier block 30 to flow into the interior of the lower fluid chamber 112 thereby achieving a hydraulic cushioning effect for the knee-joint base 10 bending through clockwise rotation.

Further, it is noted that the reason that the fluid discussed above does not flow into the lower fluid channel 13 is primarily that the fluid has to first pass the lower cruciform channel 131 to then flow into the lower fluid channel 13, and this requires an even larger pressure of the fluid. Based on the fluid dynamic principle that fluid flows toward a relatively lower site, the fluid will come out of the one end opening of the second passage 32 on the lower side of the fluid barrier block 30.

Referring to FIGS. 8-11, oppositely, when the knee-joint base 10 bends through counterclockwise rotation to restore the original condition, the principle of hydraulic cushioning is similar to that of the knee-joint base 10 bending through clockwise rotation shown in FIGS. 4-7, and as such, repeated description will be omitted herein.

The present invention forms the cushioning fluid chamber directly in the interior of the knee-joint base 10, so as to reduce cost and also to allow for direct control the knee-joint base 10 in rotation (counterclockwise or clockwise) and bending such that by means of a pressure difference between the upper fluid chamber 111 and the lower fluid chamber 112, fluid is caused to flow therebetween to realize an effect of hydraulic cushioning to for example achieve effective cushioning and reducing an impact force that a user has to take during walking, making walking posture natural and easy.

Figure 11:
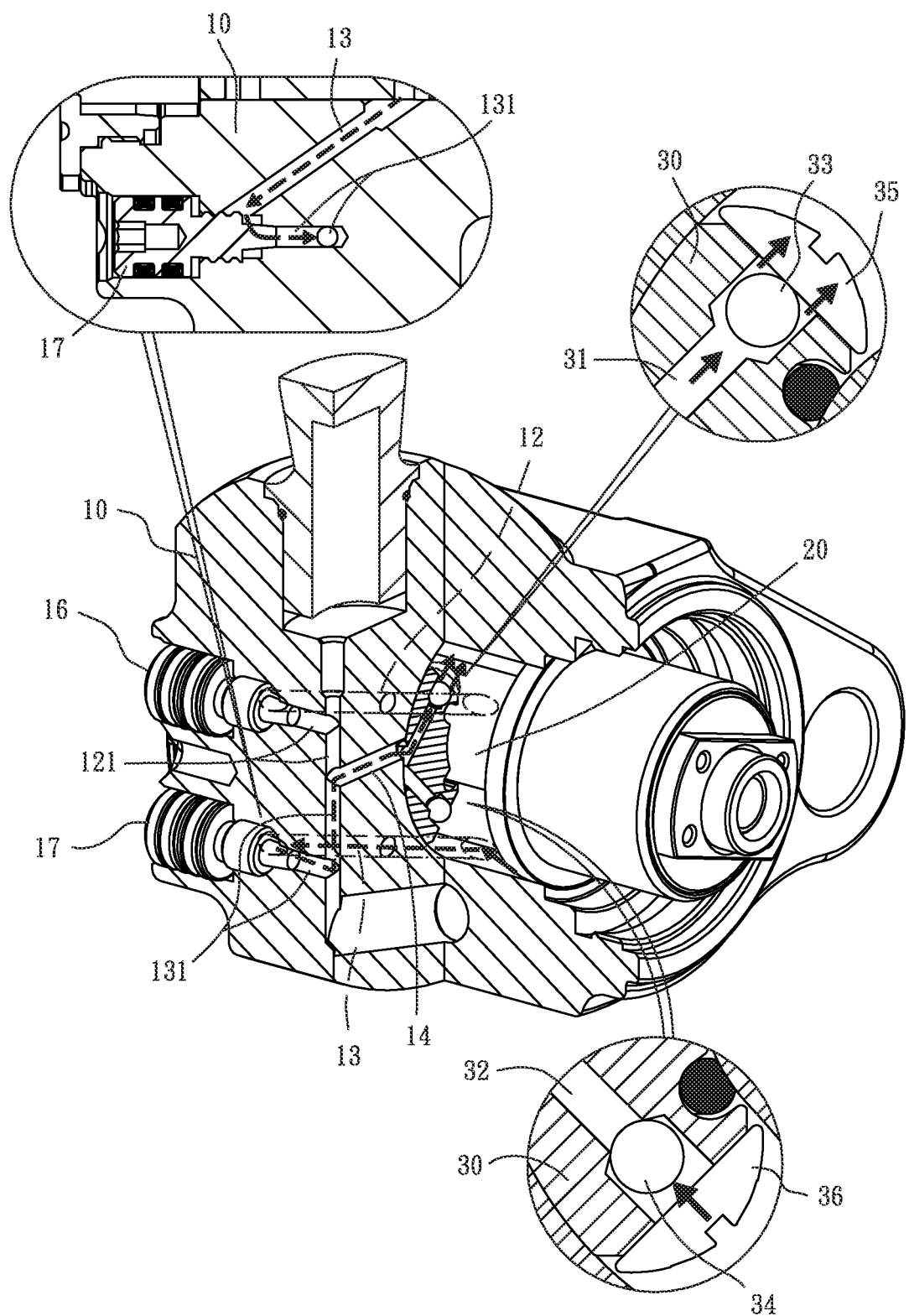
Figure 12:
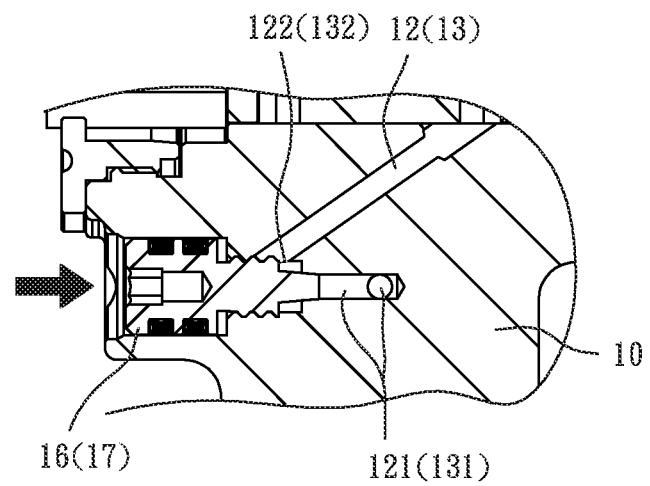
FIGS. 12 and 13 are cross-sectional views showing a regulation structure of upper and lower valve needles according to the present invention and an example of operation for regulation.
Figure 13:
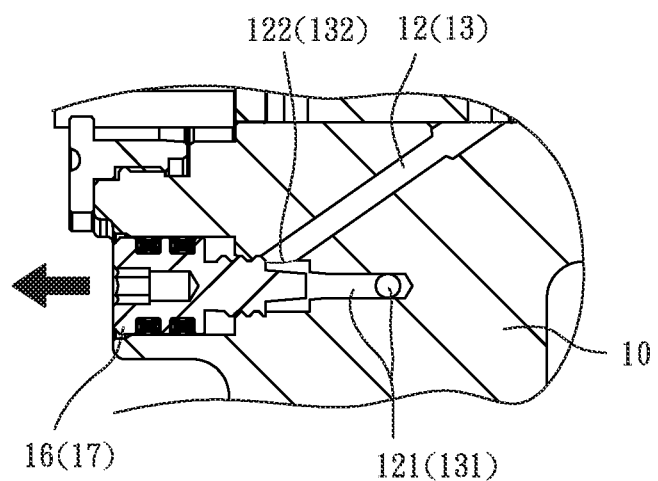

Referring to FIGS. 11, 12, and 13, in an embodiment, the knee-joint base 10 is screw-joined to an upper valve needle 16 and a lower valve needle 17, wherein an end of the upper valve needle 16 defines an opening 122 in a connecting site of the upper fluid channel 12 and the upper cruciform channel 121; and an end of the lower valve needle 17 defines an opening 132 in a connecting site of the lower fluid channel 13 and the lower cruciform channel 131.

As such, through rotating the upper valve needle 16 or the lower valve needle 17 to have it screwed inwardly or outwardly, the size of the opening 122, 132 of the upper fluid channel 12 or the lower fluid channel 13 can be adjusted to regulate the flow rate or flow speed of the fluid to thereby achieve an effect of varying the magnitude of the cushioning hydraulic pressure and speed for the knee-joint base 10 rotating (counterclockwise or clockwise) to bend.

We claim:
1. A knee joint structure featuring hydraulic control, comprising:
  a knee-joint base, the knee-joint base forming a receiving space in an interior thereof, a fluid being received in the receiving space, an upper fluid channel and a lower fluid channel being formed in an internal wall of the knee-joint base at one side of the receiving space, the upper fluid channel and the lower fluid channel being in communication with a common channel;
  a hydraulic axle core, which is arranged in the receiving space, two ends of the hydraulic axle core being each connected to one end of a link bar, an opposite end of the link bar being pivotally connected to a pivotal base; and a fluid barrier block, which is arranged on the internal wall of the knee-joint base and in contact with the hydraulic axle core to divide the receiving space into an upper fluid chamber and a lower fluid chamber, the upper fluid chamber being in communication with the upper fluid channel, the lower fluid chamber being in communication with the lower fluid channel, the fluid barrier block being in communication with the common channel and controlling the fluid to flow unidirectionally from the upper fluid chamber into the lower fluid chamber, or from the lower fluid chamber into the upper fluid chamber.

2. The knee joint structure featuring hydraulic control according to claim 1, wherein the upper fluid channel is in communication with an upper cruciform channel, and the lower fluid channel is in communication with a lower cruciform channel, and the upper cruciform channel and the lower cruciform channel are commonly in communication with the common channel.

3. The knee joint structure featuring hydraulic control according to claim 2, wherein the knee-joint base is screw-joined to an upper valve needle and a lower valve needle, an end of the upper valve needle defining an opening in a connecting site of the upper fluid channel and the upper cruciform channel, an end of the lower valve needle defining an opening in a connecting site of the lower fluid channel and the lower cruciform channel.

4. The knee joint structure featuring hydraulic control according to claim 1, wherein the fluid comprises one of a hydraulic liquid and a lubricant oil.

5. The knee joint structure featuring hydraulic control according to claim 1, wherein the two ends of the hydraulic axle core are respectively provided with two positioning members, in order to respectively connect to the ends of link bars by the positioning members.

6. The knee joint structure featuring hydraulic control according to claim 1, wherein the fluid barrier block comprises a first passage and a second passage, one end opening of the first passage being in communication with the upper fluid chamber and being provided with a first one-way valve for controlling opening and closing of the one end opening of the first passage, one end opening of the second passage being in communication with the lower fluid chamber and being provided with a second one-way valve for controlling opening and closing of the one end opening of the second passage, an opposite end opening of the first passage and an opposite end opening of the second passage being jointly in communication with the common channel.

7. The knee joint structure featuring hydraulic control according to claim 6, wherein the first one-way valve is structured such that the one end opening of the first passage is provided with a first spherical bead, the first spherical bead being movably arranged in the one end opening of the first passage, the first one-way valve further comprising a first blocking member, the first blocking member functioning to block and retain the first spherical bead; and the second one-way valve is structured such that the one end opening of the second passage is provided with a second spherical bead, the second spherical bead being movably arranged in the one end opening of the second passage for controlling opening and closing of the one end opening of the second passage, the second one-way valve further comprising a second blocking member, the second blocking member functioning to block and retain the second spherical bead.

8. The knee joint structure featuring hydraulic control according to claim 1, wherein the fluid barrier block is mounted to the internal wall of the knee-joint base by being fastened by two fastening members.

9. The knee joint structure featuring hydraulic control according to claim 1, wherein the fluid barrier block and the knee-joint base are integrally formed as a one-piece structure.

\* \* \* \* \*